United States Patent
Kikuchi et al.

(10) Patent No.: US 9,018,436 B2
(45) Date of Patent: Apr. 28, 2015

(54) ABSORBENT STRUCTURE AND ABSORBENT WEARING ARTICLE USING THE SAME

(75) Inventors: Kyo Kikuchi, Kagawa (JP); Kei Wakasugi, Kagawa (JP); Naoto Ohashi, Kagawa (JP); Osamu Ishikawa, Kagawa (JP)

(73) Assignee: Unicharm Corporation, Ehime (JP)

( * ) Notice: Subject to any disclaimer, the term of this patent is extended or adjusted under 35 U.S.C. 154(b) by 49 days.

(21) Appl. No.: 13/882,332

(22) PCT Filed: Jan. 27, 2012

(86) PCT No.: PCT/JP2012/000551
§ 371 (c)(1),
(2), (4) Date: Apr. 29, 2013

(87) PCT Pub. No.: WO2012/105211
PCT Pub. Date: Aug. 9, 2012

(65) Prior Publication Data
US 2013/0296819 A1   Nov. 7, 2013

(30) Foreign Application Priority Data
Jan. 31, 2011   (JP) .................................. 2011-019253

(51) Int. Cl.
*A61F 13/533*   (2006.01)
*A61F 13/538*   (2006.01)
*A61F 13/496*   (2006.01)

(52) U.S. Cl.
CPC ............. *A61F 13/538* (2013.01); *A61F 13/496* (2013.01); *A61F 13/533* (2013.01)

(58) Field of Classification Search
CPC .............................. A61F 13/533; A61F 13/536
USPC ..................................................... 604/379, 380
See application file for complete search history.

(56) References Cited

U.S. PATENT DOCUMENTS

| | | | | |
|---|---|---|---|---|
| 4,685,915 A | * | 8/1987 | Hasse et al. | 604/378 |
| 4,834,735 A | * | 5/1989 | Alemany et al. | 604/368 |
| 5,019,063 A | * | 5/1991 | Marsan et al. | 604/368 |
| 5,047,023 A | * | 9/1991 | Berg | 604/368 |
| 5,092,860 A | * | 3/1992 | Pigneul | 604/380 |

(Continued)

FOREIGN PATENT DOCUMENTS

| | | |
|---|---|---|
| EP | 0 325 416 | 1/1989 |
| JP | 2004-065929 | 3/2004 |

(Continued)

OTHER PUBLICATIONS

International Search Report from corresponding PCT application No. PCT/JP2012/000551 dated May 1, 2012 (1 pg).

*Primary Examiner* — Susan Su
(74) *Attorney, Agent, or Firm* — Brinks Gilson & Lione (57) ABSTRACT

An absorbent structure that includes a first region, a second region and a central region extending between the first and second regions, the first region and part of the central region are formed with a thick segment. The second region is formed with a thin segment having a thickness dimension smaller than that of the thick segment. Between the thick segment and the thin segment, a thickness-sloped segment having a thickness dimension gradually reduced from the side of the first region toward the second region and the thin segment and at least a region of the thickness-sloped segment being adjacent to the thin segment are debossed.

14 Claims, 9 Drawing Sheets

(56) References Cited

U.S. PATENT DOCUMENTS

| | | | |
|---|---|---|---|
| 5,746,729 A * | 5/1998 | Wada et al. | 604/378 |
| 6,911,574 B1 * | 6/2005 | Mizutani | 604/380 |
| 2002/0177829 A1 * | 11/2002 | Fell et al. | 604/385.01 |
| 2003/0060791 A1 * | 3/2003 | Drevik | 604/380 |
| 2006/0276766 A1 * | 12/2006 | Kentolall | 604/385.01 |
| 2006/0276767 A1 * | 12/2006 | Ueminami et al. | 604/385.31 |
| 2007/0005036 A1 * | 1/2007 | Nishikawa et al. | 604/380 |
| 2008/0294140 A1 * | 11/2008 | Ecker et al. | 604/385.23 |
| 2012/0040171 A1 * | 2/2012 | Alkmin et al. | 428/304.4 |
| 2012/0041406 A1 * | 2/2012 | Alkmin et al. | 604/383 |
| 2013/0165882 A1 * | 6/2013 | Kawakami et al. | 604/374 |
| 2013/0184665 A1 * | 7/2013 | Kato et al. | 604/374 |
| 2013/0310784 A1 * | 11/2013 | Bryant et al. | 604/385.01 |

FOREIGN PATENT DOCUMENTS

| | | |
|---|---|---|
| JP | 2006-280468 | 10/2006 |
| JP | 2010-125199 | 6/2010 |

* cited by examiner

ABSORBENT STRUCTURE AND ABSORBENT WEARING ARTICLE USING THE SAME

TECHNICAL FIELD

This disclosure relates to absorbent structures for absorbent wearing articles and more particularly to absorbent structures for disposable wearing articles such as disposable diapers, menstruation napkins and incontinent pads.

BACKGROUND

Conventionally, absorbent structures shaped to have an uneven thickness and absorbent articles using the same are well known. For example, JP 2004-65929 A (PTL 1) discloses an absorbent structure having relatively thick segments and relatively thin segments and an absorbent article using such an absorbent structure.

CITATION LIST

Patent Literature

{PTL 1}
JP 2004-65929 A

SUMMARY

Technical Problem

The absorbent article disclosed in PTL 1 is provided with an absorbent structure having locally high absorption capacity in the relatively thick segment and such relatively thick segment may be located in a region in which a relatively large amount of bodily fluids is discharged to utilize the absorption capacity of this region adequately. On the other hand, the relatively thin segment may be located in a region in which a relatively small amount of bodily fluids is discharged and thereby the total absorption efficiency of the structure can be improved.

However, a stepped boundary is formed between the thick segment and the thin segment and such stepped boundary can create a feeling of discomfort against the wearer and, in addition, the stepped boundary might locally crack to cause a leakage of bodily fluids.

An object of this invention is to provide an absorbent structure having a high absorption efficiency assured by shaping the structure to have a non-uniform thickness and having generally equal stiffness as a whole, and an absorbent wearing article using this absorbent structure.

Solution to Problem

According to a first aspect of this invention, there is provided an absorbent structure for an absorbent wearing article having a longitudinal direction and a transverse direction being orthogonal thereto and including at least a bodily fluid absorbent core, wherein:

the bodily fluid absorbent core includes a thick segment, a thin segment having a thickness dimension smaller than that of the thick segment and, between the thick segment and the thin segment, a thickness-sloped segment having a thickness dimension gradually reducing from the thick segment to the thin segment, wherein at least a region of the thickness-sloped segment adjacent to the thin segment is formed with a plurality of debosses.

According to a second aspect of this invention, there is provided an absorbent wearing article including a chassis having a topsheet, a backsheet and an absorbent structure sandwiched therebetween.

The absorbent wearing article further includes:

the chassis defining a front waist region, a rear waist region and a crotch region extending between these front and rear waist regions, wherein:

the absorbent structure extending from the front waist region to the rear waist region; and the first region of the absorbent structure lying nearer to the front waist region, the second region lies nearer to the rear waist region, and the central region corresponds to the crotch region.

DESCRIPTION OF EMBODIMENTS

Figure 1:
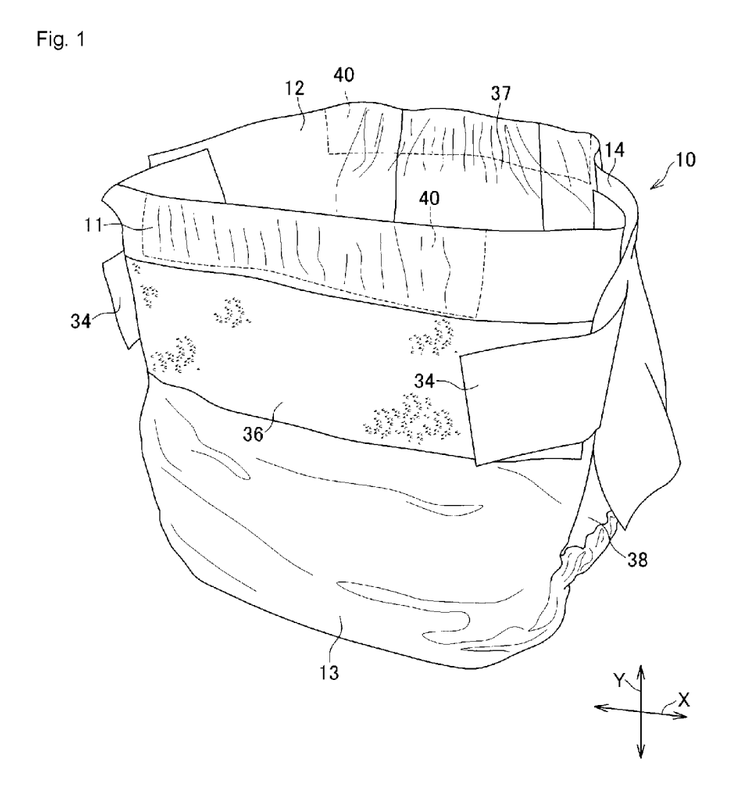
FIG. 1 is a perspective view showing a first embodiment of an absorbent wearing article using an absorbent structure according to this invention exemplarily in the form of a disposable diaper.
Figure 2:
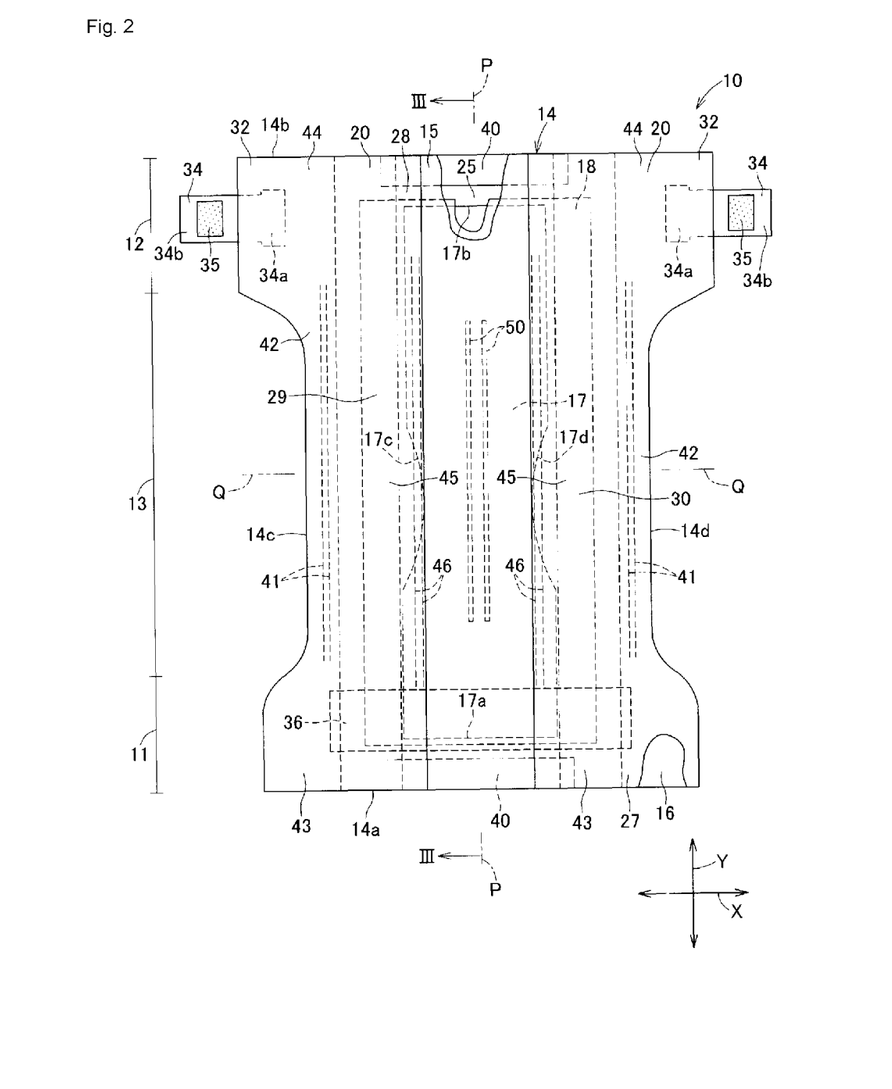
FIG. 2 is an opened plan view of the diaper according to the first embodiment.

Referring to FIGS. 1 and 2, a diaper 10 has a longitudinal axis P-P, a transverse axis Q-Q orthogonal to the longitudinal axis, a longitudinal direction Y extending in parallel to the longitudinal axis P-P, a transverse direction X extending in parallel to the transverse axis Q-Q, and includes a chassis 14 which defines a front waist region 11, a rear waist region 12 and a crotch region 13 extending between the front and rear waist regions 11, 12.

The chassis 14 includes a front end 14a, a rear end 14b, opposite side edges 14c, 14d concave curved inward in the crotch region 13, a topsheet 15 lying on a skin-facing side and a liquid-impervious backsheet 16 defining an outer surface of the diaper 10 and lying on a non-skin-facing side wherein an absorbent structure 17 is sandwiched between the topsheet 15 and the backsheet 16. Furthermore, an intermediate sheet 18 is sandwiched between the topsheet 15 and the absorbent structure 17 and a pair of containment sheets 20 is located on the skin-facing side of the diaper 10 symmetrically about the longitudinal axis P-P.

The topsheet 15 may be formed of a liquid-pervious fibrous nonwoven fabric, for example, an air-through fibrous nonwoven fabric having a basis mass in a range of about 15 to about 45 g/m$^2$, or a perforated plastic film or a laminate sheet thereof.

The backsheet 16 may be formed of a known liquid-impervious fibrous nonwoven fabric such as a spun-bonded nonwoven fabric, a point-bonded nonwoven fabric, an SMS (spunbonded/meltblown/spunbonded) nonwoven fabric each having a basis mass in a range of about 10 to about 40 g/m$^2$, liquid-impervious plastic film, or a laminate sheet thereof.

Figure 3:
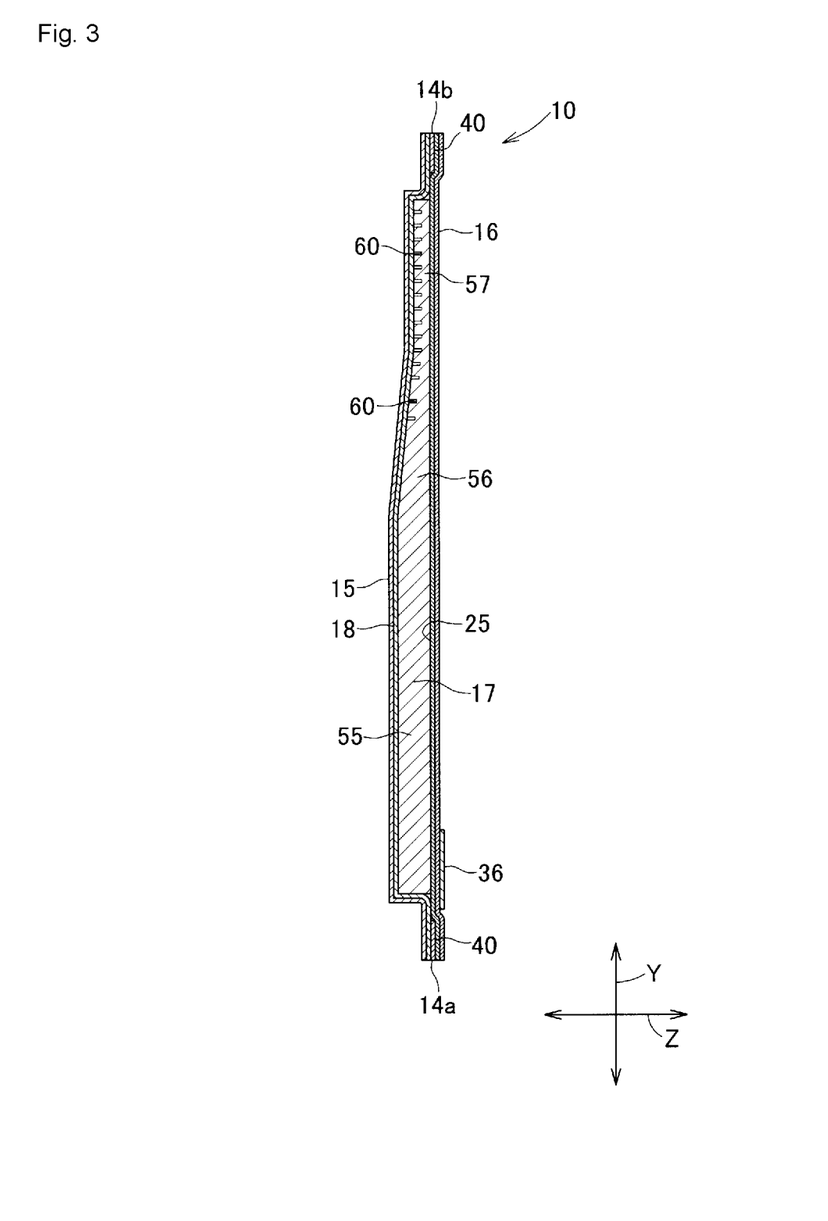
FIG. 3 is a sectional view of the diaper taken along line in FIG. 2.

The intermediate sheet 18 may be formed of a known breathable and liquid-pervious fibrous nonwoven fabric, for example, an air-through nonwoven fabric having a basis mass in a range of about 15 to about 45 g/m$^2$ and serves to improve a cushioning effect for the wearer's skin, and to prevent bodily fluids from unintentionally dispersing and to prevent bodily fluids from unintentionally flowing back toward the topsheet 15 by keeping the topsheet 15 and the absorbent structure 17 away from each other. It should be noted that the diaper 10 may not include the intermediate sheet 18.

Preferably, the containment sheets 20 may be formed of a hydrophobic fibrous nonwoven fabric, a moisture-pervious and a plastic film or a laminate sheet thereof wherein, for example, an SMS fibrous nonwoven fabric or a spunbonded fibrous nonwoven fabric having a basis mass in a range of about 10 to about 30 g/m$^2$ is useful as the nonwoven fabric for this purpose.

The absorbent structure 17 includes a liquid-absorbent core obtained by forming a mixture of superabsorbent polymer particles (SAP), fluff wood pulp fibers and optionally thermoplasticsynthetic fibers (staple fibers) in a predetermined shape and a liquid-dispersant sheet made of, for example, a liquid-pervious fibrous nonwoven fabric sheet used to wrap the liquid-absorbent core and thereby to improve shape retention and liquid dispersing ability of the liquid-absorbent core. The absorbent structure 17 is provided on a bottom surface thereof with a barrier sheet 25 formed of liquid-impervious or -resistant fibrous nonwoven fabric. It should be noted that the advantageous effects of the invention can be achieved with an absorbent structure 17 formed of the liquid-absorbent core alone, as will be described later.

The barrier sheet 25 may be formed of a breathable plastic film, a liquid-resistant SMS (spunbonded/meltblown/spunbonded) fibrous nonwoven fabric having a basis mass in a range of about 10 to about 30 g/m$^2$, spunbonded fiber nonwoven fabric or a laminate sheet thereof.

The chassis 14 has, outboard of front and rear ends 17a, 17b of the absorbent structure 17, respectively, front and rear end flaps 27, 28 extending in the transverse direction X and, outboard of opposite side edges 17c, 17d of the absorbent structure 17 in the transverse direction X, respectively, a pair of side flaps 29, 30. The front and rear end flaps 27, 28 are formed of respective extensions of the containment sheet 20, the topsheet 15, the barrier sheet 25 and the backsheet 16 extending outward in the longitudinal direction Y beyond the front and rear ends 17a, 17b of the absorbent structure 17 and stacked one upon another. The side flaps 29, 30 are formed of respective extensions of the topsheet 15, the containment sheet 20, the barrier sheet 25 and the backsheet 16 extending outward in the transverse direction X beyond the opposite side edges 17c, 17d of the absorbent structure 17 and stacked one upon another.

In respective rear ears 32 defined by crossover sites between the rear end flap 28 and respective side flaps 29, 30, proximal segment of respective ones of paired tape fastener tabs 34 are sandwiched between respective laterals of the containment sheet 20 and the backsheet 16 and affixed therebetween with hot melt adhesives applied to respective inner surfaces of the sheets 16, 20. Respective distal segments 34b of these tape fastener tabs 34 extending outward in the transverse direction X beyond respective side edges (i.e., the side edges of the rear waist region 12) are provided with a first fastening element 35 having hooks for a mechanical fastener.

With the diaper 10 put on the wearer's body, the first fastening element 35 detachably fastened to a second fastening element 36 extending on the outer surface of the front waist region 11 in the transverse direction X and having loops for the mechanical fastener and, thereupon, a waist-opening 37 and a pair of leg-openings 38 are defined (See FIG. 1).

Between the topsheet 15 and the barrier sheet 25 both partially defining the front and rear end flaps 27, 28, a waist band 40 formed of an elastic belt made of urethane foam or the like having a interconnected cell is sandwiched. Between the backsheet 16 and each of the containment sheets 20 both partially defining the side flaps 29, 30, two leg elastic elements 41 formed of elastic strands or elastic strings are sandwiched and bonded therebetween under a tension and in a contractible manner in the longitudinal direction Y with hot melt adhesive (not shown) applied to the respective inner surfaces of these sheets 16, 20.

The containment sheets 20 respectively have proximal edges 42 partially defining the side flaps 29, 30, front and rear end segments 43, 44 bonded to the skin-facing side of the topsheet 15 in the front and rear waist regions 11, 12 and to the skin-facing side of the backsheet 16 extending outward in the transverse direction X beyond the side edges of the topsheet 15 and with hot melt adhesive, and distal edges 45 extending in the longitudinal direction Y between the front and rear affixed end segments 43, 44 and formed by folding inward the inner side edges of the respective containment sheet 20. The distal edges 45 are respectively provided with a plurality of elastic elements 46 formed of elastic strands or elastic strings extending in the longitudinal direction Y and attached thereto under a tension and in a contractible manner in the longitudinal direction Y. With the diaper put on the wearer's body, the distal edges 45 are spaced upward from the skin-facing side of the topsheet 15 under the contraction of the elastic elements 46 so as to form a pair of barriers adapted to prevent body waste from leaking sideways.

In the crotch region 13, the inner surface of the barrier sheet 25 facing the non-skin-facing side of the absorbent structure 17 is provided with a plurality of linear indicator means 50 extending in the longitudinal direction Y. The indicator means 50 are formed of an ink layer adapted to discolor when it is wetted with bodily fluids, such as urine, so that such discoloration can be visually recognized from the outside. Though not shown, it is possible to sandwich a coversheet impregnated with a required amount of surfactant between the indicator means 50 and the barrier sheet 25 and thereby to facilitate the indicator means 50 to be visually recognized.

Figure 4:
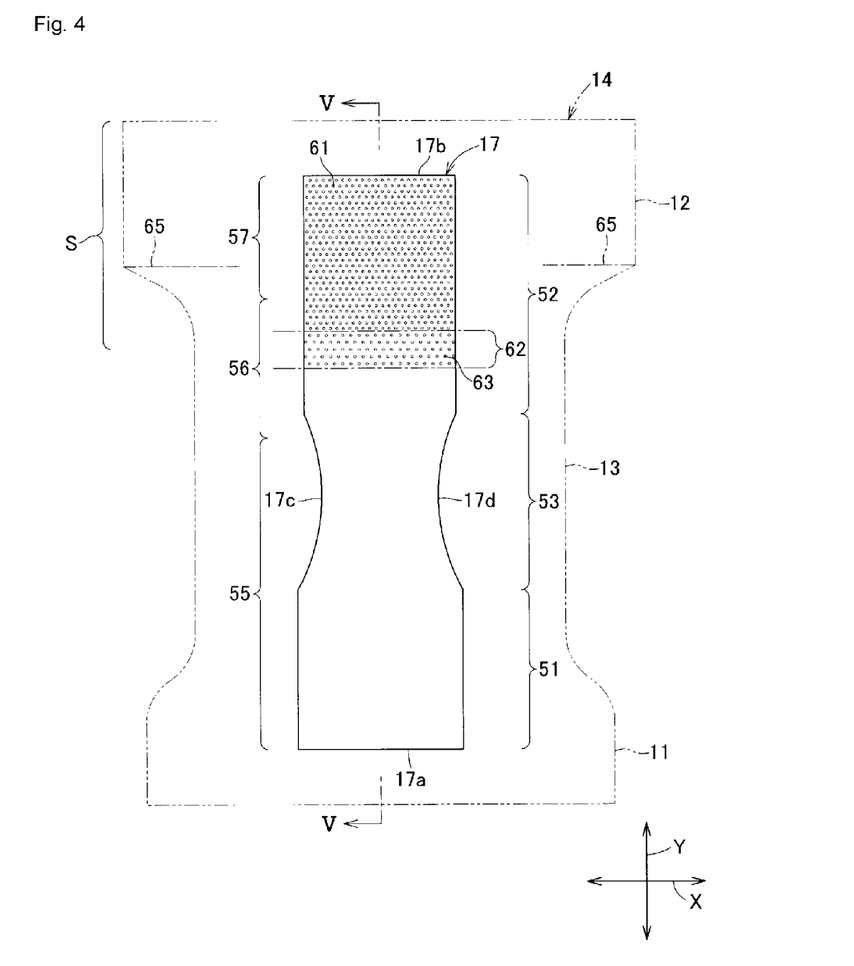
FIG. 4 is a plan view of the absorbent structure of FIG. 1 wherein an outer shape of the diaper is indicated by an imaginary line.
Figure 5:
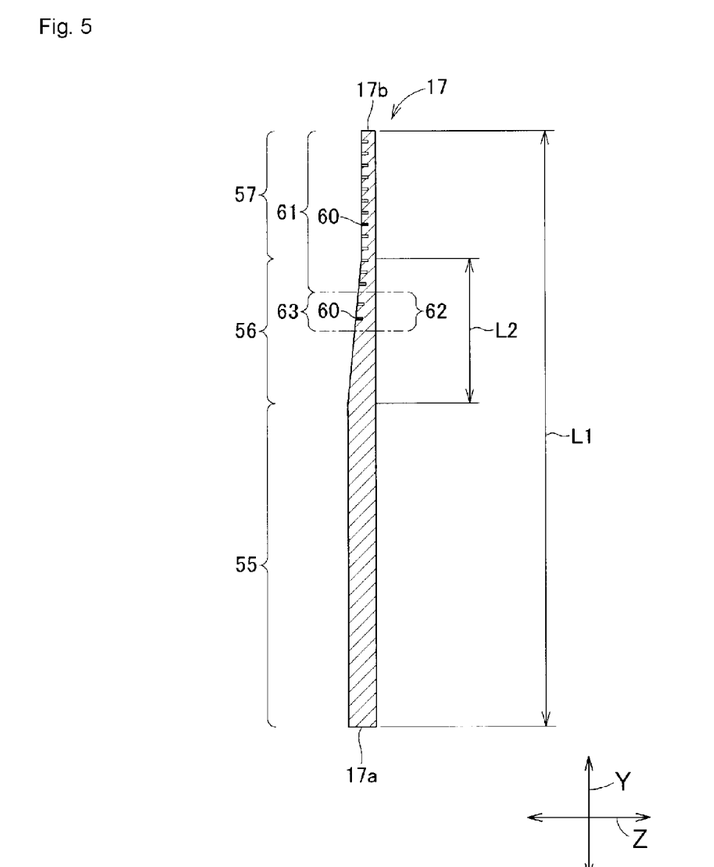
FIG. 5 is a sectional view taken along line V-V in FIG. 4.

Referring to FIGS. 3 through 5, the absorbent structure has a front region (first region) 51 lying on near the front waist region 11, a rear region (second region) 52 and a central region 53 extending between the front region 51 and the rear region 52 and defined between the inwardly curving segments of the opposite side edges 17c, 17d. In the absorbent structure 17, the front region 51 is thicker than the rear region 52 and, more specifically, the absorbent structure 17 includes a relatively thick segment 55 extending from the front region 51 to the central region 53, a thickness-sloped segment 56 extending rearward from the relatively thick segment 55 to be gradually sloped toward the bottom side of the absorbent structure 17 and a relatively thin segment 57 extending from the thickness-sloped segment 56 to the rear end 17b. While the absorbent structure 17 is formed of a single layer continuously extending in the longitudinal direction Y in this embodiment, it is possible to form the relatively thick segment 55 by two layers to make this segment 55 thicker than the remaining segments or to form the absorbent structure 17 as a whole inclusive of the relatively thin segment 57 by two or more layers.

It should be noted, however, that the absorbent structure 17 formed as a whole by a single layer, according to the illustrated embodiment is more advantageous than the structure formed of two or more layers with respect to the shape retention because the fluff wood pulp fibers and optionally added thermoplastic fibers are well commingled.

While the absorbent single layer structure 17 may be shaped using known methods or equipment, the absorbent structure 17 may alternatively be shaped by the method described below.

<Method of Making the Thick Segment 55, the Thickness-Sloped Segment 56 and the Thin Segment 57>

In an apparatus (not shown) including a conduit to feed absorbent materials such as fluff wood pulp fibers and/or superabsorbent polymer particles and a rotating drum formed with a plurality of depressions for accumulation and adapted to be conveyed in a machine direction below the duct, the absorbent materials are fed from the duct into the depressed molds for accumulation so that the absorbent materials may be accumulated in the respective molds to form an aggregation (or a mass) (i.e., the liquid-absorbent core). The drum is of a mesh-like construction such that bottoms of the respective molds are formed with a plurality of openings through which the absorbent materials may be sucked into the molds and accumulated therein. A depth dimension of each mold for accumulation (a length dimension from the upper surface of each mold to the bottom of each mold for accumulation) depends on whether each mold is used to form the thick segment 55, the thickness-sloped segment 56 or the thin segment 57. More specifically, the thick segment 55 of the absorbent structure 17 is formed in the molds each having a relatively small depth dimension, the thin segment 57 is formed in the molds each having a relatively large depth dimension and thickness-sloped segment 56 is formed in a group of the molds arranged between the thick segment 55 and the thin segment 57 and each having a sloped depth. In the region including the molds each having the large depth dimension, the mesh opening space is preferably adjusted to be larger than in the region including the molds each having the small depth dimension to assure that a correspondingly smaller and a desired quantity of the absorbent materials can be accumulated therein. In the region including the molds each having a sloped bottom used to form the thickness-sloped segment 56, it is preferred to vary the mesh opening space of the respective molds continuously.

As described above, the absorbent structure 17 as a whole has a peculiar shape defined by uneven thickness wherein bodily fluids, primarily urine discharged by the wearer can be reliably absorbed in the thick segment 55 having a required absorptive capacity on the front waist region 11. The rear waist region 12 in which the amount of excreted bodily fluids is usually smaller than in the front waist region 11 is formed with the thin segment 57 and therefore substantially all segments in the absorbent structure 17 as a whole serve to absorb bodily fluids. In consequence, the absorbent structure according to this invention has higher absorption efficiency than that of conventional absorbent structures shaped and arranged to uniform its absorption capacity. In addition, an amount of absorbent material for the liquid-absorbent core can be reduced to the minimum necessary and thereby production cost can be correspondingly kept down.

Formation of the thickness-sloped segment 56 and the thin segment 57 makes the thickness of the absorbent structure 17 gradually reduced from the crotch region 13 toward the rear waist region 12 and consequently the rear waist region 12 is smoothly deformed along the wearer's body shape so that the rear waist region 12 may fit to the wearer's body, and improving the feeling to the wearer of the diaper. Furthermore, a thickness of the diaper 10 as a whole is reduced and the individual diaper 10 can be folded into two so that the front and rear waist regions 11, 12 can be put flat together without becoming bulky, enabling a set of the diapers 10 to be neatly packaged.

In the conventional absorbent structure 17 including the thick segment 55 and the thin segment 57 being directly adjacent and contiguous to each other, an abrupt variation of the thickness direction causes a significant stiffness difference and a stepped boundary between the thick segment 55 and the thin segment 57. In consequence, such stepped boundary might create a feeling of discomfort against the wearer and, in addition, the absorbent structure 17 might be partially bent and/or twisted to induce leakage of bodily fluids. In contrast, according to this embodiment, the thickness-sloped segment 56 is formed between the thick segment 55 and the thin segment 57 and thereby the thickness dimension is gently varied to avoid the significant stiffness difference and the stepped boundary due to the abrupt change of the thickness dimension. In this way, the structure would not create a feeling of discomfort against the wearer and would not be bent and/or twisted to induce leakage of bodily fluids in vicinities of boundaries of the respective segments 55, 56, 57.

The thin segment 57 is preferably formed in the region not exposed to a large quantity of excreted bodily fluids. Specifically, the thin segment of the absorbent structure 17 is preferably formed in a zone S of the diaper 10 extending from the rear waist region 12 so that the thin segment 57 may occupy between 35% to 45% of a total area of the absorbent structure 17. To prevent the problem that the stiffness difference and the stepped boundary formed due to the abrupt variation of the thickness might create a feeling of discomfort against the wearer, a length dimension L2 of the thickness-sloped segment 56 in the longitudinal direction Y is preferably in a range of about 20 to about 150 mm, more preferably in a range of about 50 to about 110 mm on the assumption that a length dimension L1 of the absorbent structure 17 in the longitudinal direction Y is in a range of about 320 to about 450 mm. If less than about 20 mm, the length dimension L2 of the thickness-sloped segment 56 in the longitudinal direction Y will be insufficient to form a gentle slope between the thick segment 55 and the thin segment 57 and thereby to alleviate the thickness difference between these two segments. As a result, a step might be created in the vicinity of the boundary between the thick segment 55 and the thickness-sloped segment 56 and create a feeling of discomfort against the wearer. If the length dimension L2 of the thickness-sloped segment 56 in the longitudinal direction Y exceeds 150 mm, an area of the thick segment 55 in the absorbent structure 17 as a whole might become insufficient to achieve the effect of this embodiment, specifically, to assure a desired bodily fluid absorption capacity substantially by the thick segment 55.

Now it will be described below how to form the respective segments 55, 56, 57 of the absorbent structure 17. The thick segment 55 has a thickness dimension in a range of about 2.7 to about 3.3 mm and the liquid-absorbent core in this segment 55 may be formed of a mixture of fluff wood pulp fibers having a basis mass in a range of about 220 to about 260 g/m$^2$ and SAP (super absorbent polymer particles) having a basis mass in a range of about 140 to about 180 g/m$^2$. The thin segment 56 has a thickness dimension in a range of about 2.2 to about 2.8 mm and the liquid-absorbent core in this segment 56 may be formed of a mixture of fluff wood pulp fibers having a basis mass in a range of about 180 to about 220 g/m² and SAP having a basis mass in a range of about 140 to about 180 g/m². In this manner, the basis mass is lower in the thin segment 57 than in the thick segment 55. Specifically, the basis mass of the liquid-absorbent core in the thin segment 57 is preferably in a range of about 50 to about 85% of the basis mass of the thick segment 55 to achieve the above-described effect of this invention.

The thickness dimension of the respective segments in the absorbent structure 17 may be measured by use of PEACOCK Thickness Tester (measuring pressure: 12.5 g/cm²). More specifically, the absorbent structure 17 may be taken out from the diaper 10, then the regions of the structure 17 respectively corresponding to the thick segment 55 and the thin segment 57 are cut in a size of about 50 mm in the longitudinal direction Y and about 50 mm in the transverse direction X to obtain test pieces and thickness in the midsections of the respective test pieces are measured by the Thickness Tester.

As will be seen in FIG. 4, in the rear region 52 of the absorbent structure 17, the thin segment 57 is formed with first debossed zone 61 in which a plurality of debosses approximately arranged in a zigzag-pattern as viewed in the longitudinal direction Y of the absorbent structure 17 and an adjacent region 62 of the thickness-sloped segment 56 to the thin segment 57 is formed with a second debossed zone 63 in which a plurality of debosses arranged in zigzag-pattern as viewed in the a longitudinal direction Y of the absorbent structure 17. Under the effect of the first and second debossed zones 61, 63, the thin segment 57 and the adjacent region 62 of the thickness-sloped segment 56 to the thin segment 57 have respective stiffness higher than the respective stiffness if they were not debossed in this manner.

As has previously been described, according to this embodiment, the thickness of the absorbent structure 17 is adjustably sloped to define the segments having the absorption capacities different one from another and, if none of appropriate countermeasures is taken, such arrangement might result in a stiffness difference between each pair of the adjacent segments. To reduce such stiffness difference, the thickness-sloped segment is formed between the thick segment 55 and the thin segment 57 and, in addition, the first and second debossed zones 61, 63 are formed to enhance the stiffness of the thin segment 57 and the adjacent region 62 of the thickness-sloped segment 56 thereto so that deformation and/or shape collapse of the absorbent structure 17 due to its partial crack can be further reliably prevented. In the absorbent structure including the thin segment 57, during use of such absorbent structure, the shape of this thin segment would otherwise readily collapse to cause leakage of bodily fluids. However, the thin segment 57 may be previously debossed to avoid such disadvantageous situation.

A plurality of the debosses 60 defining the first and second debossed zones 61, 63 have a generally uniform sized circular shape and arranged closely together in the first debossed zone 61 and less closely together in the second debossed zone 63. In consequence, a total occupancy area percentage of the debosses 60 in the first debossed zone 61 as a whole is higher than a total area occupancy percentage of the debosses 62 in the second debossed zone 63 as a whole. Specifically, the total area occupancy percentage of the debosses 60 in the first debossed zone 61 is in a range of about 12 to about 18% while the total area occupancy percentage of the debosses 60 in the second debossed zone 63 is in a range of about 5.0 to about 9.0%. A length dimension of the respective debosses 60 in the thickness direction Z (i.e., depth) is in a range of about 0.2 to about 0.5 mm. It should be appreciated here that specific values of the total area occupancy percentage may be appropriately varied, that the debossing pattern is not limited to the zigzag-pattern but may be appropriately selected from various patterns and that the shape of the deboss 60 also is not limited to the circular shape but may be appropriately selected from various shapes such as oval, rhombic and reed shapes, so far as the above-described correlation can be assured.

The debosses 60 are arranged more closely and at the correspondingly higher total area occupancy percentage thereof in the first debossed zone 61 than in the second debossed zone 63 as has been described above to distinguish a stiffness change occurring in the thin segment 57 from a stiffness change occurring in the adjacent region 62 of the thickness-sloped segment 56 to the thin segment 57 so that the stiffness values of the thin segment 57 and the adjacent region 62 of the thickness-sloped segment 56 thereto may be regulated to be substantially equal to each other. In this way, the first and second debossed zones 61, 63 formed in the thin segment 57 and the adjacent region 62 of the thickness-sloped segment 56 thereto, respectively, allow the stiffness value of the absorbent structure 17 as a whole to be substantially uniform. With the diaper 10 put on the body, the absorbent structure 17 is thus more resistant to being wrinkled and deformed or twisted than it would otherwise be, even if the crotch region 13 is wrinkled due to the movement of the wearer's legs.

While the regions to be formed with the first and second debossed zones 61, 63, respectively, may be appropriately designed depending on the respective stiffness values of the thickness-sloped segment 56 and the thin segment 57 and/or the stiffness difference between these two segments and the thick segment 55, anyone of the first and second debossed zones 61,63 is preferably formed in the vicinity of a border line 65 between the crotch region 13 and the rear waist region 12 to traverse this border line 65 longitudinally. This is for the reason that the portion of the absorbent structure 17 lying in the crotch region 13 is always kept in contact with the wearer's thighs and inguinal regions and apt to be affected by an external force due to the movement of the wearer's body. In other words, it may be empirically predicted that the absorbent structure 17 is most likely to be deformed or twisted in the vicinity of the borderline 65 between the above-mentioned portion and the rear waist region 12. Therefore, to assure a stiffness sufficient to prevent the thickness-sloped segment 56 and/or the thin segment 57 from being deformed or twisted in the vicinity of the border line 65, it is preferred to deboss the above-defined portion of the absorbent structure 17.

Figure 6:
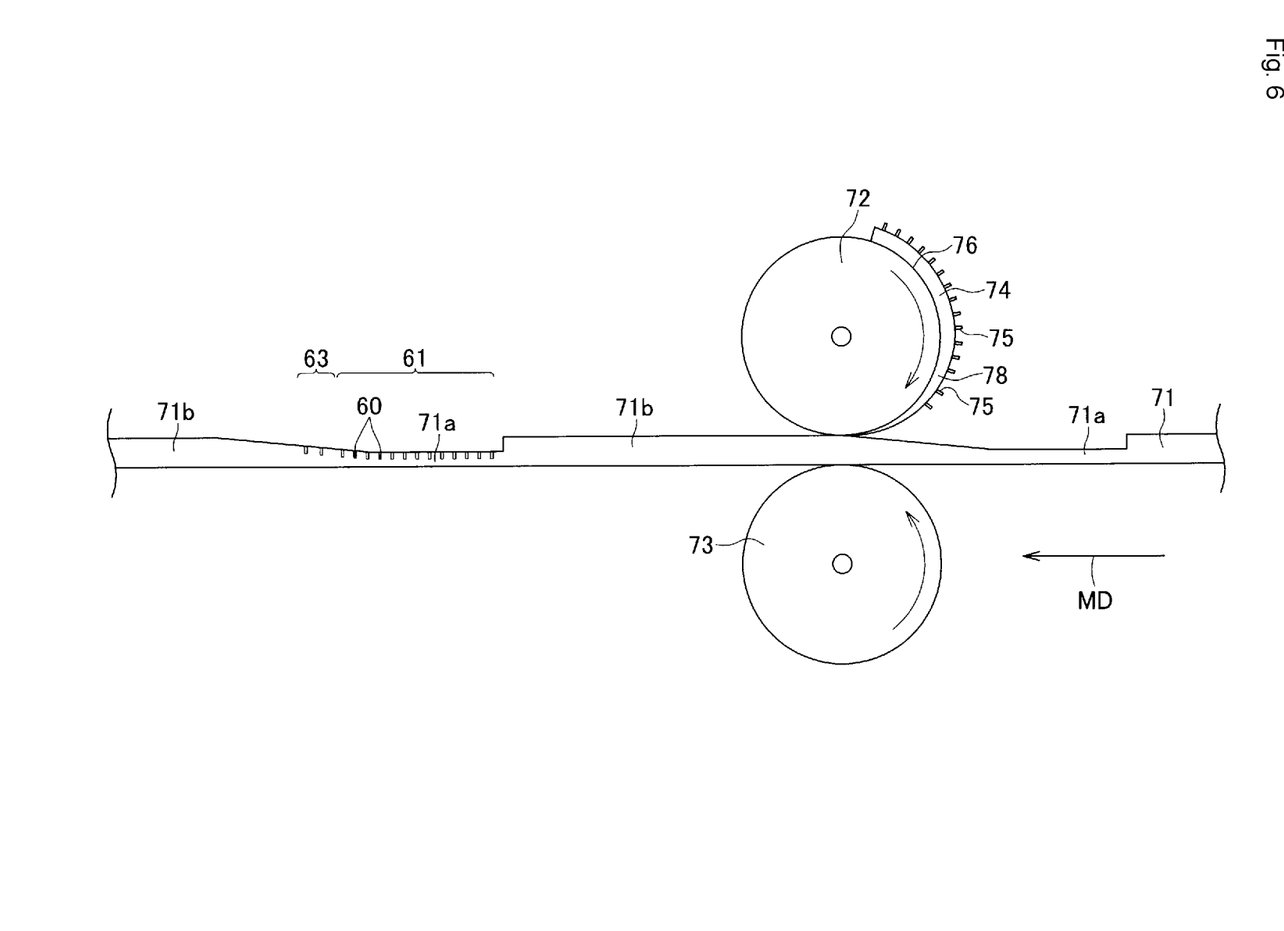
FIG. 6 is a side view of the diaper of FIG. 1 partially illustrating a process of making the absorbent structure.

Referring to FIG. 6, there is illustrated an apparatus and method that may be used to perform debossing to provide the absorbent structure of the invention. A contiguous absorbent structure 71 corresponding to a plurality of absorbent structures 17 is conveyed by a conveyor rolls (not shown) in a machine direction MD. The contiguous absorbent structure 71 is formed by wrapping monolayer or multilayer liquid-absorbent cores with a liquid-absorbent core wrapping sheet wherein respective portions 71a corresponding to the thin segments 57 and respective portions 71b correspond to the thick segments 55.

Figure 7:
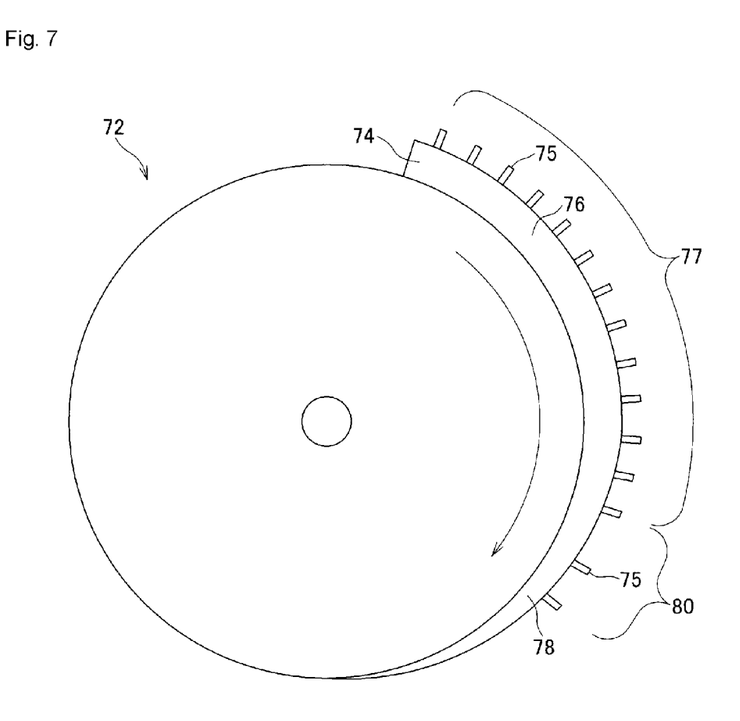
FIG. 7 is a side view illustrating a debossing roll to form the absorbent structure of FIG. 1.

A step of debossing involves a clockwise rotating debossing roller 72 above the contiguous absorbent structure 71, and a counterclockwise rotating anvil roll 73 located to face the debossing roller 72 and having a smooth outer peripheral surface. The outer peripheral surface of the debossing roller 72 is partially formed with a raised area 74 having a thickness gradually increasing in its circumferential direction and a plurality of debossing pins 75 projecting from the surface of this raised area 74. The debossing pins 75 are divided into a first group of debossing pins 77 formed in a thick sub-area 76 of the raised area 74 corresponding to the first debossed zone 61 of the individual absorbent structure 17 and a second group of the debossing pins 80 formed in a thin sub-area 78 of the raised area 74 corresponding to the second debossed zone 63 of the individual absorbent structure 17 wherein the second group of the debossing pins 80 are arranged more sparsely than the first group of the debossing pins 77. To assure that the contiguous absorbent structure 71 is stably formed with the debosses 60, it is possible to heat the debossing pins 75 at a temperature properly controlled so that the sheet member constituting the contiguous absorbent structure 71 might not be sealed around the debossing pins 75.

Rotational velocity of the debossing roller 72 and conveyance velocity of the contiguous absorbent structure 71 are controllably synchronized with each other so that the raised area 74 may reliably face the respective portions 71a of the contiguous absorbent structure 71 corresponding to the thickness-sloped segment 56 and the thin segment 57. In this way, the first group of the debossing pins 77 arranged in the thick sub-area 76 of the raised area 74 presses the region corresponding to the thin segment 57 to form the first debossed zone 61 and the second group of the debossing pins 80 arranged in the thin sub-area 78 presses the region corresponding to the thickness-sloped segment 56 to form the second debossed zone 63. A dimension by which the debossing roller 72 and the anvil roll 73 are spaced from each other is adjusted so that the portion of the outer peripheral surface of the debossing roller 72 not formed with the raised area 74 may be kept out of contact with a portion 71b of the contiguous absorbent structure 71 corresponding to the thick segment 55.

According to this embodiment, one and the same debossing roller 72 is formed with the raised area 74 so that the first and second debossed zones 61, 62 having different patterns may be concurrently formed and thereby the production process may be simplified in comparison with the case in which two debossing rollers are used for the respective debossed zones 61, 63. In addition, the thickness of the raised area 74 is varied depending on the shapes of the respective regions of the contiguous absorbent structure 71 to be pressed and therefore there is no anxiety that the thickness-sloped segment 56 might be pressed at a relatively high pressure and have a high stiffness beyond necessity. The thin segment 57 is pressed by the thick sub-area 76 of the raised area 74 so that the thin segment 57 may have a desired stiffness and may be formed in a desired small thickness.

The step of debossing can be carried out by a debossing roller having arrangement other than that of the debossing roller as has been described above. Specifically, it is possible to use the debossing roller in which the first and second groups of the debossing pins 77, 80 are similar to each other so far as the total area occupancy percentage if the debossing pins 75 is concerned but different from each other so far as a length dimension of the debossing pin is concerned, more specifically, the debossing pin 75 in the first group of the debossing pins 77 has the length dimension larger than that of the debossing pin 75 in the second group of the debossing pins 80 and creates correspondingly higher stiffness than that created by the debossing pin 75 in the second group of the debossing pins 80. It is also possible to use two debossing rollers respectively have different debossing patterns so that the ranges corresponding to the first and second debossed zones 61, 63 are debossed by one of the debossing rollers and then the region corresponding to the first debossed zone 61 is further debossed by the other of the debossing rollers.

<Method of Measuring the Bending Stiffness of Respective Segments 55, 57 of the Absorbent Structure 17>

Bending stiffness of the respective segments 55, 57 in the absorbent structure 17 may be measured by a tapered bending stiffness tester. Specifically, the absorbent structure 17 may be taken out from the diaper 10, then from the regions of the structure 17 respectively corresponding to the thick segment 55 and the thin segment 57, generally rectangular pieces each in a size of about 70 mm in the longitudinal direction Y and about 38.1 mm in the transverse direction X are cut out to obtain test pieces. Using the tester, tapered bending stiffness of the respective segments may be measured with the test pieces being bent in the transverse direction X.

TABLE 1 in the following paragraph indicates stiffness values (N) of the thick segment 55 and the thin segment 57, stiffness difference (N) between these stiffness values measured with a constituent ratio of the pulp fiber and SAP in the absorbent structure 17 being varied, and a result of shape retention test based on occurrence degree of cracks and/or tears in the absorbent structure.

TABLE 1

| | Thick section | | Thin section | | Stiffness value A of thick section (N) | Stiffness value B of thin section (N) | Stiffness difference between A and B (N) | Result of shape retention test (N) |
|---|---|---|---|---|---|---|---|---|
| | Basis mass of pulp fiber (g/m²) | Basis mass of SAP (g/m²) | Basis mass pulp fiber (g/m²) | Basis mass of SAP (g/m²) | | | | |
| Inventive Example 1 | 250 | 200 | 200 | 160 | 0.11 | 0.10 | 0.01 | good |
| Inventive Example 2 | 200 | 160 | 160 | 128 | 0.09 | 0.08 | 0.01 | good |
| Inventive Example 3 | 150 | 120 | 120 | 96 | 0.08 | 0.07 | 0.01 | good |
| Comparative Example 1 | 250 | 200 | 200 | 160 | 0.12 | 0.07 | 0.05 | poor |
| Comparative Example 2 | 250 | 200 | 200 | 160 | 0.12 | 0.16 | −0.04 | average |

Referring to TABLE 1, the absorbent structure 17 according to the Inventive Examples 1 to 3, pulp fiber and SAP respectively have basis mass (g/m²) different from each other in the segment 55 as well as in the segment 57. The absorbent structure 17 according to the Comparative Example 1 is similar to the absorbent structure 17 according to the Inventive Example 1 so far as its composition is concerned but both the thickness-sloped segment 56 and the thin segment 57 have not been subjected to debossing working. The absorbent structure 17 according to the Comparative Example 2 also is similar to the absorbent structure 17 according to the Inventive Example 1 so far as its composition is concerned but distinguished therefrom in that the thickness-sloped segment 56 and the thin segment 57 have been debossed at a relatively high pressure so as to have a relatively high stiffness value.

<Method of Measuring the Shape Retention>

The diapers respectively using the absorbent structures according to the Inventive Examples 1 to 3, and the Comparative Examples 1 and 2 as test samples were put on ten test subjects and degree of shape collapse such as occurrence of cracks and/or torn regions in the liquid-absorbent core after urination was observed. The measurement was conducted on ten babies each having an average baby body weight in a range of about 6 to about 11 kg and consisting of five baby girls and five baby boys so that a male-female ratio may be 1:1. The measurement result was visually evaluated as follows: the liquid-absorbent core in which neither partial crack nor partial tear can be visually recognized was evaluated as "good"; the liquid-absorbent core in which partial cracks and/or partial tears can be observed was evaluated as "average"; and the liquid-absorbent core in which the cracks and/or tears continuously extend in the transverse direction X and the core is substantially segmented was evaluated as "poor".

As will be apparent from TABLE 1 indicating the measurement result, in the Inventive Examples 1-3, a stiffness difference between the thick segment 55 and the thin segment 57 was unexceptionally 0.01N, practically zero even when the pulp fiber and SAP respectively have basis masses different from each other and the result of the shape retention test was unexceptionally "good". In the Comparative Example 1, the thin segment 57 was not subjected to the debossing working and, as a result, a stiffness difference between the thick segment 55 and the thin segment 57 was as large as 0.05N and the result of the shape retention test was "poor". In the Comparative Example 2, the first debossed zone 61 of the thin segment 57 was worked at a relatively high pressure and consequently a stiffness value of the thin segment 57 exceeded the stiffness value of the thick segment 55. Specifically, a stiffness difference between the thick segment 55 and the thin segment 57 was as large as −0.04N (in contrast with the cases of the other Inventive Examples and Comparative Example, this minus stiffness difference value was represented by the value obtained by subtracting the stiffness value of the thick segment 55 from the stiffness value of the thin segment 57). The result of the shape retention test was "average".

In the light of the measurement result, a cantilever bending resistance difference between the thick segment 55 and the thin segment 57 is preferably 0.04N or less in order to prevent the liquid-absorbent core from partially cracking and/or tearing. The cantilever bending resistance difference between the thick segment 55 and the thin segment 57 may be set to 0.04N or less in this manner to eliminate the anxiety that the liquid-absorbent core might partially cracking and/or tearing during use of the diaper 10 and thereby it is possible to prevent the thin segment 57 from becoming shapeless. The wearer is free from a feeling of stiffness difference and gets the sensation as if the absorbent structure put on the wearer's body has substantially uniform thickness. The wearer can be released from a sense of anxiety that the absorbent structure 17 might be deformed and/or the absorption performance of the absorbent structure 17 due to thinness of the thin segment 57.

<Segmentation of the Absorbent Structure 17 into the Respective Segments 55, 56, 57>

A method for segmentation of the absorbent structure 17 to define the thick segment 55, the thickness-sloped segment 56 and the thin segment 57 will be exemplarily described hereunder. It should be noted that the method described herein is adapted to be executed before the absorbent structure 17 is subjected to the deboss-working and based not on the thickness dimension but on the basis mass of the respective segments. Effectiveness of such method is supported by the fact that no change occurs in the basis masses of the respective segments 55, 56, 57 before and after subjected to the deboss-working and, in addition, the basis mass depends on the thickness dimension as has previously been described.

First of all, the absorbent structure 17 having a length dimension of about 360 mm in the longitudinal direction is divided into eighteen (18) sections each having a length dimension of about 20 mm in the longitudinal direction Y. Then a basis mass basis mass value of the section having the highest basis mass is set as 1 and ratios of basis mass values of the other sections to the maximum basis mass value 1 are calculated and these calculated values are plotted into a table in which the sections 1 to 18 are orderly arranged. Of the respective points plotted in this manner, when both of lines connecting a certain point to the adjacent points on both sides of this point define falling gradients, these two points are designated as boundary points. The boundary point lying on the side of the thick segment (the side on which the basis mass ratio to the maximum basis mass value is relatively high) is designated as a first boundary point defined between the thick segment 55 and the thickness-sloped segment 56 and the boundary point lying near the thin segment (the side on which the basis mass ratio to the maximum basis mass value is relatively low) is designated as a second boundary point. In this manner, the absorbent structure 17 may be segmented into the thickness-sloped segment 56 defined by a segment having a length dimension between the respective sections defining the respective boundary points, the thick segment 55 extending from the first boundary point toward the thick side and the thin segment 57 extending from the second boundary point toward the thin side.

Figure 8:
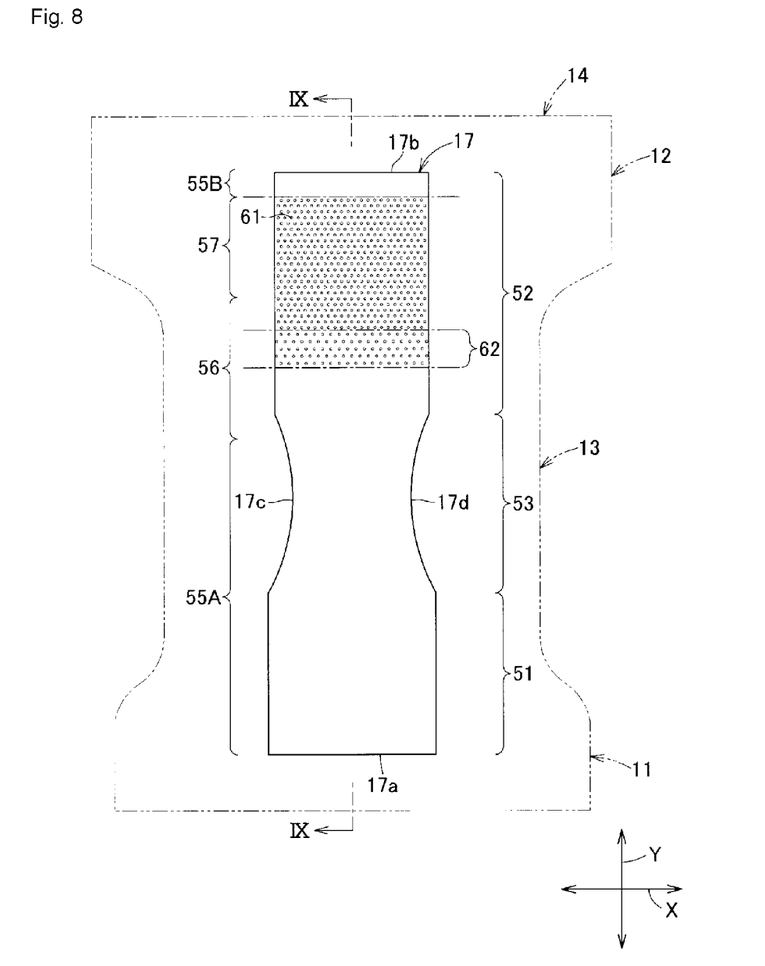
FIG. 8 is a view similar to FIG. 4, showing the absorbent structure in a diaper according to a second embodiment of this invention.
Figure 9:
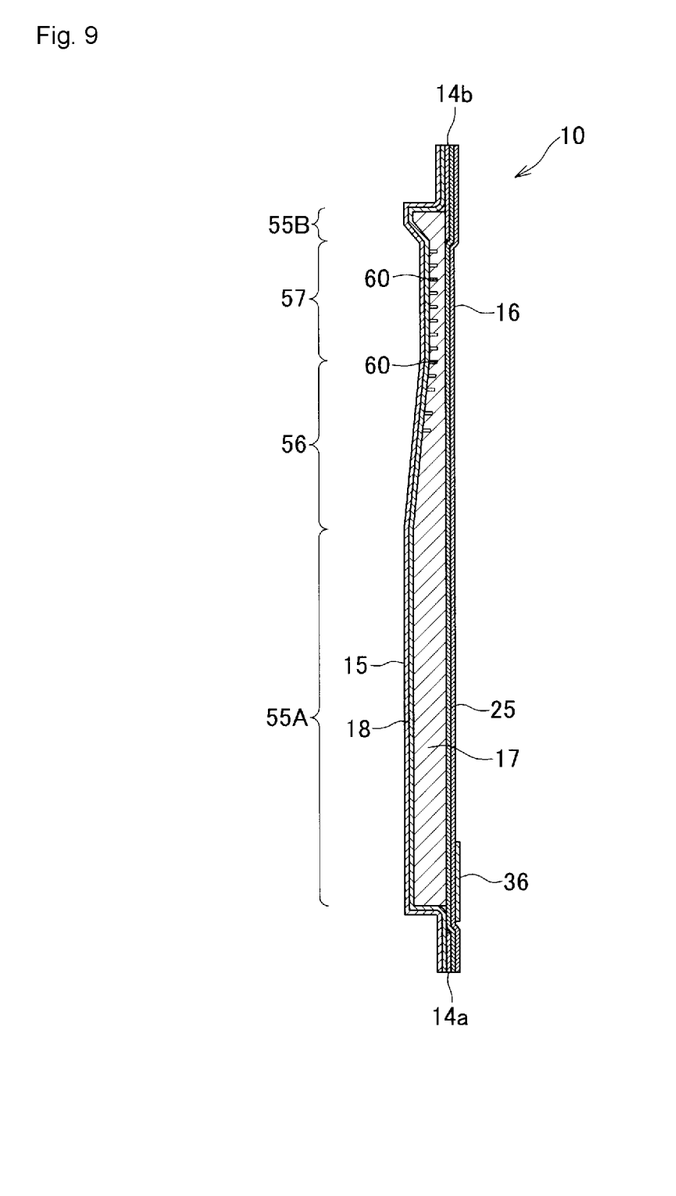
FIG. 9 is a sectional view of the absorbent structure taken along line IX-IX in FIG. 8.

Referring to FIGS. 8 and 9, basic construction of the diaper 10 according to this embodiment is similar to that of the first embodiment and therefore only the features distinguished from the first embodiment will be described below.

According to this embodiment, the absorbent structure 17 includes a first thick segment 55A extending from the front region 51 to a rear portion of the central region 53, the thin segment 57 defined in the rear region 52, the thickness-sloped segment 56 extending between the first thick segment 55A and the thin segment 57 and a second thick segment 55B lying between the thin segment 57 and the rear end 17b of the absorbent structure 17.

The second thick segment 55B has a thickness dimension substantially equal to that of the first thick segment 55A or a thickness dimension at least 1.1 times or more of the thickness dimension of the thick segment 57 and not formed with the first debossed zone 61. The second thick segment 55b having the thickness dimension substantially equal to that of the first thick segment 55A formed on the side of the rear end 17b of the rear region 52 in this manner assures that a quantity of bodily fluids not adequately absorbed by the thin segment 57 in the vicinity of the second thick segment 55B can be absorbed and retained by the second thick segment 55B and, in consequence, leakage of bodily fluids beyond the rear end 17b can be reliably prevented.

It should be appreciated that the absorbent structure according to this invention can be used not only for the disposable diaper but also for the other various types of bodily fluid absorbent article such as menstruation napkin, incontinent pad and toilet-training pants. The component members of the diaper 10 are not limited to those described in this specification but the other various types of material widely used in the relevant technical field may be used without limitation. The terms "first" and "second" used in the specification and claims of the present invention are used merely to distinguish the similar elements, similar positions or the other similar means.

The first aspect of the present invention may be arranged in at least the following features:

(1) An absorbent structure for an absorbent wearing article has a longitudinal direction and a transverse direction being orthogonal thereto and includes at least a bodily fluid absorbent core, wherein:

the bodily fluid absorbent core includes a thick segment, a thin segment having a thickness dimension smaller than that of the thick segment and, between the thick segment and the thin segment, a thickness-sloped segment having a thickness dimension gradually reducing from the thick segment to the thin segment, wherein at least a region of the thickness-sloped segment adjacent to the thin segment is formed with a plurality of debosses.

The aspect of the present invention described in (1) may include at least the following embodiments:

(i) The thin segment is formed with a first debossed zone including a plurality of debosses and the thickness-sloped segment is formed with a second debossed zone including a plurality of debosses wherein the debosses are more closely arranged in the first debossed zone than in the second debossed zone.

(ii) The bodily fluid absorbent core is a monolayer bodily fluid absorbent core.

(iii) The monolayer bodily fluid absorbent core is wrapped in a liquid dispersant sheet.

(iv) A difference between a tapered bending stiffness value of the thick segment along a given dimension in the transverse direction and a tapered bending stiffness value of the thin segment along a given dimension in the transverse direction is 0.04N or less.

(v) A basis mass of the bodily fluid absorbent core in the thick segment is higher than a basis mass of the bodily fluid absorbent core in the thin segment and a basis mass of the bodily fluid absorbent core in the thickness-sloped segment depends on a gradient of the thickness slope.

(vi) A length dimension of the absorbent structure in the longitudinal direction is in a range of about 320 to about 450 mm, a length dimension of the thickness-sloped segment in the longitudinal direction is in a range of about 20 to about 150 mm.

(vii) The basis mass of the thin segment is in a range of 50 to 85% of a basis mass of the thick segment.

(viii) The bodily fluid absorbent core further includes a second thick segment extending outward in the longitudinal direction from the thin segment wherein the first thick segment has a thickness dimension equal to that of the second thick segment.

(ix) The thin segment occupies between 35 to 45% of the total area of the bodily fluid absorbent core.

(x) The length in the longitudinal direction of the thickness-sloped segment is between 20 to 150 mm.

(xi) The length of the thickness-sloped segment in the longitudinal direction is between 50 to 110 mm.

(xii) The absorbent structure has a length between 320 to 450 mm.

(xiii) The absorbent structure has inwardly curving segments on of opposite side edges with the absorbent structure comprising a first region, a second region and a central region extending between the first region and the second region, the central region being defined as the region between the inwardly curving segments of the opposite side edges, wherein a first region and part of the central region are formed with the thick segment and the thickness sloped section extends into both the central region and the second region.

(2) A second aspect of the present invention may be arranged in at least the following features:

An absorbent wearing article includes a chassis having a topsheet, a backsheet and an absorbent structure sandwiched therebetween.

The absorbent wearing article further includes:

the chassis defining a front waist region, a rear waist region and a crotch region extending between these front and rear waist regions, wherein:

the absorbent structure extending from the front waist region to the rear waist region; and the first region of the absorbent structure lying nearer to the front waist region, the second region lies nearer to the rear waist region, and the central region corresponds to the crotch region.

The described aspects and/or embodiments provide one or more of the following effects.

(a) The thickness-sloped segment is formed to extend between the thick segment and the thin segment and thereby formation of the stepped boundary due to an abrupt variation in the thickness dimension may be avoided. A portion of the thickness-sloped segment and the thin segment are debossed to enhance the stiffness in these regions. In consequence, a noticeable stiffness difference would not develop overall and the absorbent structure would not partially crack and/or tear due to a change in stiffness or creation of stepped boundary even if the absorbent structure is bent during use thereof.

(b) The thick segment of the absorbent structure lies in the front waist region in which urination occurs so that the absorbent structure may fully exert its absorption performance. The thin segment lying in the rear waist region improves fitness to the wearer's buttocks and, in addition, contributes to improvement in the absorption efficiency of the absorbent structure as a whole.

Further advantageous effects of the respective embodiments may be obtained as discussed in the respective related descriptions.

This application claims the benefit of Japanese Application No. 2011-019253 the entire disclosure of which is incorporated by reference herein.

The invention claimed is:

1. An absorbent structure for an absorbent wearing article having a longitudinal direction and a transverse direction being orthogonal thereto and including at least a bodily fluid absorbent core, wherein:

the bodily fluid absorbent core includes a thick segment, a thin segment having a thickness dimension smaller than that of the thick segment and, between the thick segment and the thin segment, a thickness-sloped segment having a thickness dimension gradually reducing from the thick segment to the thin segment, wherein at least a region of the thickness-sloped segment adjacent to the thin segment is formed with a plurality of debosses, wherein the thin segment is formed with a first debossed zone including a plurality of debosses and the thickness-sloped segment is formed with a second debossed zone including a plurality of debosses wherein the debosses are more closely arranged in the first debossed zone than in the second debossed zone.

2. The absorbent structure defined by claim 1, wherein the bodily fluid absorbent core is a monolayer bodily liquid-absorbent core.

3. The absorbent structure as defined by claim 2, wherein the monolayer bodily liquid-absorbent core is wrapped in a liquid dispersant sheet.

4. The absorbent structure defined by claim 1, wherein a difference between a tapered bending stiffness value of the thick segment along a given dimension in the transverse direction and a tapered bending stiffness value of the thin segment along a given dimension in the transverse direction is 0.04N or less.

5. The absorbent structure defined by claim 1, wherein a basis mass of the bodily fluid absorbent core in the thick segment is higher than a basis mass of the bodily fluid absorbent core in the thin segment and a basis mass of the bodily fluid absorbent core in the thickness-sloped segment depends on a gradient of the thickness slope.

6. The absorbent structure defined by claim 1, wherein a length dimension of the absorbent structure in the longitudinal direction is in a range of about 320 to about 450 mm, a length dimension of the thickness-sloped segment in the longitudinal direction is in a range of about 20 to about 150 mm.

7. The absorbent structure defined by claim 6, wherein the basis mass of the thin segment is in a range of 50 to 85% of a basis mass of the thick segment.

8. The absorbent structure defined by claim 1, wherein the bodily fluid absorbent core further comprises a second thick segment extending outward in the longitudinal direction from the thin segment wherein the first thick segment has a thickness dimension equal to that of the second thick segment.

9. The absorbent structure defined by claim 1, wherein the thin segment occupies between 35 to 45% of the total area of the bodily fluid absorbent core.

10. The absorbent structure defined by claim 1, wherein the length in the longitudinal direction of the thickness-sloped segment is between 20 to 150 mm.

11. The absorbent structure defined by claim 1, wherein the length of the thickness-sloped segment in the longitudinal direction is between 50 to 110 mm.

12. The absorbent structure defined by claim 1 having a length between 320 to 450 mm.

13. The absorbent structure defined by claim 1 having inwardly curving segments on of opposite side edges with the absorbent structure comprising a first region, a second region and a central region extending between the first region and the second region, the central region being defined as the region between the inwardly curving segments of the opposite side edges, wherein a first region and part of the central region are formed with the thick segment and the thickness sloped section extends into both the central region and the second region.

14. An absorbent wearing article comprising a chassis having a topsheet, a backsheet and the absorbent structure as claimed in claim 1 sandwiched therebetween, further comprising the chassis defining a front waist region, a rear waist region and a crotch region extending between these front and rear waist regions, wherein:
  the absorbent structure extends from the front waist region to the rear waist region; and
  the first region of the absorbent structure lies nearer to the front waist region, the second region lies nearer to the rear waist region, and the central region corresponds to the crotch region.

\* \* \* \* \*